United States Patent
Colombo et al.

(10) Patent No.: US 10,723,710 B2
(45) Date of Patent: Jul. 28, 2020

(54) PROCESS FOR THE PREPARATION OF DIAMINOPHENOTHIAZINIUM COMPOUNDS HAVING A HIGH DEGREE OF PURITY

(71) Applicant: ICROM S.P.A., Milan (IT)

(72) Inventors: Matteo Colombo, Milan (IT); Paola Daverio, Milan (IT); Stella Borrelli, Milan (IT)

(73) Assignee: ICROM S.P.A., Milan (IT)

(*) Notice: Subject to any disclaimer, the term of this patent is extended or adjusted under 35 U.S.C. 154(b) by 0 days.

(21) Appl. No.: 16/301,070

(22) PCT Filed: May 16, 2017

(86) PCT No.: PCT/IB2017/052868
§ 371 (c)(1),
(2) Date: Nov. 13, 2018

(87) PCT Pub. No.: WO2017/199162
PCT Pub. Date: Nov. 23, 2017

(65) Prior Publication Data
US 2019/0185440 A1    Jun. 20, 2019

(30) Foreign Application Priority Data
May 17, 2016  (IT) ................. 10201650744

(51) Int. Cl.
C07D 279/18    (2006.01)
C09B 21/00     (2006.01)
C09B 67/54     (2006.01)

(52) U.S. Cl.
CPC ............ *C07D 279/18* (2013.01); *C09B 21/00* (2013.01); *C09B 67/0096* (2013.01)

(58) Field of Classification Search
CPC .................................................. C07D 279/18
USPC ............................................................ 544/36
See application file for complete search history.

(56) References Cited

U.S. PATENT DOCUMENTS

| | | | |
|---|---|---|---|
| 8,440,821 B2 | 5/2013 | Wischik et al. |
| 8,765,942 B2 | 7/2014 | Feraud et al. |
| 8,815,850 B2 | 8/2014 | Feraud et al. |
| 9,227,945 B2 | 1/2016 | Feraud et al. |
| 9,242,946 B2 | 1/2016 | Storey et al. |
| 9,382,220 B2 | 7/2016 | Wischik et al. |

FOREIGN PATENT DOCUMENTS

WO    WO2007110627 A2    10/2007

*Primary Examiner* — Kahsay Habte
(74) *Attorney, Agent, or Firm* — King & Schickli, PLLC

(57) ABSTRACT

A process for the preparation of diaminophenothiazinium compounds is described, which allows achieving quickly and effectively a high degree of purity of the same.

11 Claims, 1 Drawing Sheet

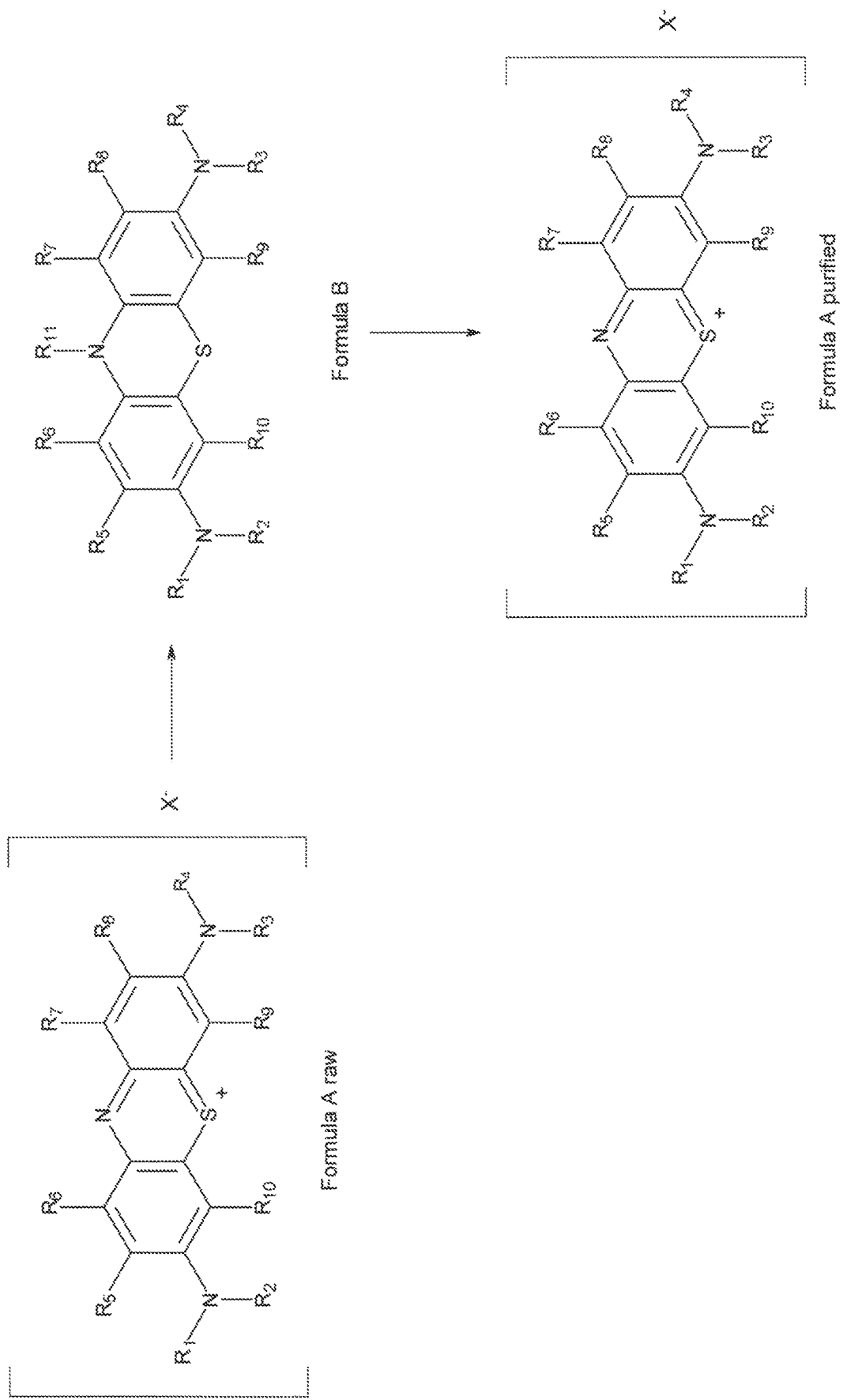

PROCESS FOR THE PREPARATION OF DIAMINOPHENOTHIAZINIUM COMPOUNDS HAVING A HIGH DEGREE OF PURITY

FIELD OF THE INVENTION

The present invention relates to a process for the preparation of diaminophenothiazinium compounds, which allows achieving quickly and effectively a high degree of purity of the same.

PRIOR ART

Colorants having a diaminophenothiazinium structure are well known. Among them, the best known is methylthioninium chloride (3,7-bis(dimethylamino)-5-phenothiazinium chloride) commonly known as methylene blue and used in an increasing number of medical applications in addition to its historical usage. One of its possible resonance structures is described in Formula I:

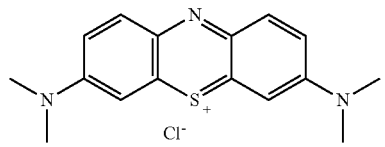

Formula I

In the medical field, methylene blue is used as an antidote in poisoning by cyanide, methemoglobinemia-inducing agents (such as phenacetin, nitrites, aniline, sulfonamides), and carbon monoxide. It is also used as a chromodiagnostic or chromoendoscopy agent. Recently, its use has been proposed for the treatment of neurodegenerative diseases, viral infections, bipolar disorders and as a tracer of the lymphatic system.

The original process for the synthesis of methylene blue was developed in 1877 (German patent number 1886, Badische Anilin-und Soda Fabrik). Over the years, the process has been revised and improved, but it is still based on the use of a large number of reagents and metal catalysts based on iron, chromium, zinc, aluminium, copper, manganese and zinc. The methylene blue contamination by metal species is therefore one of the issues and constraints to the use of this substance in the medical field.

Industrially produced methylene blue also has the problem of some organic impurities resulting from the demethylation of dimethylamine groups present in position 3 and 5 in the phenothiazine structure. Such impurities are commonly referred to as "Azure" and are described in Formula II:

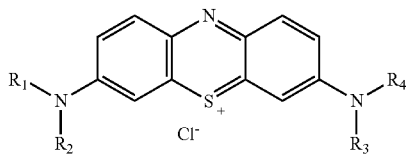

Formula II

Azure A: $R_1 = R_2 = H$, $R_3 = R_4 = Me$
Azure B: $R_1 = H$, $R_2 = R_3 = R_4 = Me$
Azure C: $R_1 = R_2 = R_3 = H$, $R_4 = Me$ The use of methylene blue in the medical field requires a limitation of both metal impurities and of organic impurities, as defined by the current Pharmacopoeias (e.g. *European Pharmacopoeia and United States Pharmacopeia*).

The purification of methylene blue from metal impurities and from Azure derivatives has no simple resolution due to the sequestering effect of the diaminophenothiazinium structure and to the chemical analogy of organic contaminants.

The same applies to the purification of Azure derivatives that are used as dyes in diagnostics.

The modified Wright-Giemsa staining is normally used to stain peripheral blood smears. The quick variant of Wright Giemsa staining uses Azure B and eosin, in the presence of phosphate buffer. Being positively charged, Azure B (blue/purple colour) is specific to the acidic cellular structures, such as nucleic acids and nucleoproteins, basophil granules and acidic proteins, neutrophil granules (weakly acidic).

An object of the present invention therefore is to provide a process for the preparation of diaminophenothiazinium compounds, which allows achieving quickly and effectively a high degree of purity of the same.

SUMMARY OF THE INVENTION

Said object is achieved by a process for the preparation of diaminophenothiazinium compounds as claimed in claim 1.

BRIEF DESCRIPTION OF THE FIGURES

The characteristics and the advantages of the present invention will become apparent from the following detailed description, from the working examples provided for illustrative purposes, and from the annexed Figures, wherein FIG. 1 shows a preparation scheme of the invention.

DETAILED DESCRIPTION OF THE INVENTION

The invention therefore relates to a process for the preparation of diaminophenothiazinium compounds having a high degree of purity, said process comprising the steps of:

1) providing a crude diaminophenothiazinium compound of formula A:

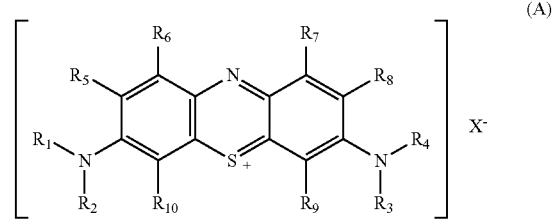

(A)

wherein $R_1$, $R_2$, $R_3$, $R_4$ are, independently of one another,
a saturated or unsaturated, linear, branched, or cyclic, C1-C6 alkyl group, optionally substituted with one or more functional groups selected from a halogen atom, a C1-C4 alkoxy, a C1-C4 alkyloxycarbonyl, or —$CONH_2$,
an aryl group optionally substituted with one or more functional groups selected from a C1-C4 alkyl group, a halogen atom, a C1-C4 alkoxy, a C1-C4 alkyloxycarbonyl, or —$CONH_2$, or
a hydrogen atom,
$R_5$, $R_6$, $R_7$, $R_8$, $R_9$, $R_{10}$ are, independently of one another, a hydrogen atom, a saturated or unsaturated, linear, branched, or cyclic, C1-C6 alkyl group, optionally substituted with one or more functional groups selected from a halogen atom, a C1-C4 alkoxy, a C1-C4 alkyloxycarbonyl, or —CONH$_2$, an aryl group optionally substituted with one or more functional groups selected from a C1-C4 alkyl group, a halogen atom, a C1-C4 alkoxy, a C1-C4 alkyloxycarbonyl, or —CONH$_2$, or a halogen atom, and wherein X$^-$ is an organic or inorganic anion, 2) synthesizing a compound of formula B:

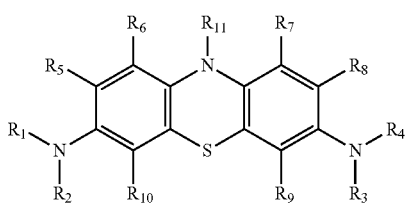

(B)

wherein R$_1$-R$_{10}$ are as in formula A,

R$_{11}$ is a hydrogen atom, a carbonyl or thiocarbonyl group functionalized with a phenyl or benzyl group, optionally substituted with C1-C4 alkyl groups, a halogen atom, C1-C4 alkoxy, or a nitro group, a C1-C8 alkyl group, linear, branched or cyclic, a C1-C8 alkylamino group, a C1-C8 alkoxy group, or a phenyloxy or benzyloxy group, optionally substituted on the aromatic ring with C1-C4 alkyl groups, a halogen atom, C1-C4 alkoxy, or a nitro group, by reaction of the crude diaminophenothiazinium compound of formula A with a reducing agent and a protective agent comprising the group R$_{11}$, and 3) obtaining a diaminophenothiazinium compound of Formula A, through oxidation of the compound of Formula B by a stable free radical agent, said stable free radical agent being proxyl (2,2,5,5-tetramethyl-1-pyrrolidinyloxy), 3-carboxyl-proxyl, 3-carbamoyl-proxyl, 2,2-dimethyl-4,5-cyclohexyl-proxyl, 3-oxo-proxyl, 3-hydroxylimine-proxyl, 3-aminomethyl-proxyl, 3-methoxy-proxyl, 3-t-butyl-proxyl, 3-maleimido-proxyl, 3,4-di-t-butyl-proxyl, 3-carboxylic-2,2,5,5-tetramethyl-1pyrrolidinyloxy, TEMPO (i.e. 2,2,6,6-tetramethyl-1-piperidinyloxy), NHAc-TEMPO, 4-Cl-6-alkyloxy-TEMPO, 4-benzoxyloxy-TEMPO, 4-methoxy-TEMPO, 4-carboxylic-4-amino-TEMPO, 4-chloro-TEMPO, 4 hydroxylimine-TEMPO, 4-hydroxy-TEMPO, 4-oxo-TEMPO, 4-oxo-TEMPO-ethylene ketal, 4-amino-TEMPO, 2,2,6,6-tetraethyl-1-piperidinyloxy, 2,2,6-trimethyl-6-ethyl 1-piperidinyloxy, di-t-butyl nitroxide, di-t-butyl nitroxyl, diphenyl nitroxide, diphenyl nitroxyl, t-butyl-t-amyl nitroxide, DOXYL (4,4-dimethyl-1-oxazolidinyloxy), 2-di-t-butyl-doxyl, 5-decane-doxyl, 2-cyclohexane-doxyl, 2,5-dimethyl-3,4-dicarboxylic-pyrrole, 2,5-dimethyl-3,4-diethylester-pyrrole, 2,3,4,5-tetraphenyl-pyrrole, 3-cyano-pyrroline-3-carbamoyl-pyrrole, 3-carboxylic-pyrroline, 1,1,3,3-tetramethylisoindoline-2-yloxyl, 1,1,3,3-tetraethylisoindolin-2-yloxyl, 5-cyclohexyl porphyrexide nitroxyl, 2,2,4,5,5-pentamethyl-[DELTA]3-imidazoline-3-oxide-1-oxyl, galvinoxyl, 1,3,3-trimethyl-2-azabicyclo[2,2,2]octane-5-one-2-oxide, 1-azabicyclo[3,3,1]nonane-2-oxide, 2-Azaadamantane N-Oxyl (AZADO), 9-Azabicyclo[3.3.1]nonane N-oxyl (ABNO), 9-Azanoradamantane N-oxyl (Nor-AZADO), or a mixture thereof.

In preferred embodiments, said crude diaminophenothiazinium compound of Formula A is selected from crude methylene blue, methylene blue double salt of zinc and mixtures thereof.

Preferably, said stable free radical agent is TEMPO (i.e. 2,2,6,6-tetramethyl-1-piperidinyloxy), NHAc-TEMPO, 4-Cl-6-alkyloxy-TEMPO, 4-benzoxyloxy-TEMPO, 4-methoxy-TEMPO, 4-carboxylic-4-amino-TEMPO, 4-chloro-TEMPO, 4 hydroxylimine-TEMPO, 4-hydroxy-TEMPO, 4-oxo-TEMPO, 4-oxo-TEMPO-ethylene ketal, 4-amino-TEMPO, 2,2,6,6-tetraethyl-1-piperidinyloxy, 2,2,6-trimethyl-6-ethyl 1-piperidinyloxy, 1,3,3-trimethyl-2-azabicyclo[2,2,2]octane-5-one-2-oxide, 1-azabicyclo[3,3,1]nonane-2-oxide, 2-Azaadamantane N-Oxyl (AZADO), 9-Azabicyclo[3.3.1]nonane N-oxyl (ABNO), 9-Azanoradamantane N-oxyl (Nor-AZADO), or a mixture thereof.

In preferred embodiments, said stable free radical agent is TEMPO (i.e. 2,2,6,6-tetramethyl-1-piperidinyloxy), NHAc-TEMPO, 4-methoxy-TEMPO, 4-carboxylic-4-amino-TEMPO, 4-chloro-TEMPO, 4 hydroxylimine-TEMPO, 4-hydroxy-TEMPO, 4-oxo-TEMPO, 4-amino-TEMPO, 2-Azaadamantane N-Oxyl (AZADO), 9-Azabicyclo[3.3.1]nonane N-oxyl (ABNO), 9-Azanoradamantane N-oxyl (Nor-AZADO), or a mixture thereof.

In particularly preferred embodiments, said stable free radical agent is TEMPO (i.e. 2,2,6,6-tetramethyl-1-piperidinyloxy), 4-hydroxy-TEMPO, 2-Azaadamantane N-Oxyl (AZADO) or a mixture thereof.

In the most preferred embodiments, said stable free radical agent is 4-hydroxy-TEMPO. Preferably, step 2) is carried out at temperatures of 10 to 60° C., more preferably at room temperature.

Preferably, step 2) is a one-pot synthesis step. This means that the reaction of the crude diaminophenothiazinium compound of formula A with a reducing agent and a protective agent comprising the group R$_{11}$ to obtain a compound of formula B takes place in a single reaction environment, or in a single container or reactor.

In this way, it is possible to avoid using long processes of separation and purification of the intermediates products obtained, thereby saving not only time but also resources (equipment, chemicals, solvents, etc.). Moreover, as a result, the chemical yield can be increased, having reduced intermediate substance losses.

Preferably, step 3) is carried out at temperatures of −10 to 20° C., more preferably 0 to 5° C.

In preferred embodiments, prior to step 3), the compound of formula B is purified by adding a chelating agent, such as ethylenediaminetetraacetic acid (EDTA) or a salt thereof, and then recrystallized. The addition of the chelating agent allows eliminating by extraction any metals present in the reaction environment.

Preferably, said stable free radical agent is the only oxidizing agent used in step 3) of the process of the invention.

Preferably, in step 3), said stable free radical agent is added to the reaction in a solid form or as an aqueous solution.

In preferred embodiments, said aqueous solution comprises up to 60% by weight of stable free radical agent. More preferably, said aqueous solution comprises 10-50% by weight of stable free radical agent.

In particularly preferred embodiments, said aqueous solution comprises 20-40% by weight of stable free radical agent.

Even more preferred are aqueous solutions comprising 20-40% by weight of stable free radical agent selected from TEMPO (i.e. 2,2,6,6-tetramethyl-1-piperidinyloxy), 4-hydroxy-TEMPO, 2-Azaadamantane N-Oxyl (AZADO) and mixtures thereof.

Preferably, in the crude diaminophenothiazinium compound of formula A, $X^-$ is an organic or inorganic anion selected from chloride, bromide, iodide, zinc chloride double salt, sulphate, phosphate, nitrate, acetate, trifluoroacetate, oxalate, tartrate, succinate, malate, fumarate, gluconate, citrate, maleate, ascorbate, benzoate, $OH^-$, and combinations thereof.

In the crude diaminophenothiazinium compound of formula A obtained by the process described above, $X^-$ is the same anion of the starting crude diaminophenothiazinium compound or it is different, but anyway selected from those listed above.

Preferably, said reducing agent is selected from sodium dithionite, sodium borohydride, methylhydrazine, hydrazine, hydrazine hydrate, ascorbic acid, formic acid, hydrogen, oxalic acid, dithiothreitol, phosphites, hypophosphites and mixtures thereof.

In preferred embodiments, said reducing agent is sodium dithionite.

Preferably, said protective agent comprising the group $R_{11}$ is selected from benzoyl chloride, benzoic anhydride, methylbenzoyl chloride, benzoyl bromide, methylbenzoyl bromide, dimethylbenzoyl chloride, chlorobenzoyl chloride, dichlorobenzoyl chloride, methoxybenzoyl chloride, nitrobenzoyl chloride, acetyl chloride, acetic anhydride, propionyl chloride, propionic anhydride, di-tert-butyl dicarbonate, benzylchloroformiate, ethylchloroformiate and mixtures thereof.

At the end of step 3), the protective agent comprising the group $R_{11}$ is removed by washing with suitable solvents, such as methyl isobutyl ketone, toluene, acetone, dichloromethane, diisopropyl ether, methyl tertbutyl ether, or a mixture thereof.

In a preferred embodiment, methylene blue double salt of zinc (MB zds) is provided, which is reduced in aqueous solution with sodium dithionite and then protected with benzoylation in a two-phase system using tetrabutylammonium bromide as a phase transfer catalyst. N-benzoyl-Leuco-methylene blue (briefly N-Bz-LMB) is thus obtained. Preferably, N-Bz-LMB is purified by treatment with EDTA to remove metals and subsequently by heat treatment with 2-propanol.

N-Bz-LMB is then hydrolysed and oxidized by using 4-hydroxy-TEMPO in aqueous HCl at low temperatures.

The resulting product is recovered from the reaction mixture by precipitation and washing, preferably with methyl isobutyl ketone and acidic water. Methylene blue is preferably recrystallized from water, more preferably acidified water, and dried.

Preferably, step 3) is a one-pot synthesis step. This means that the hydrolysis and oxidation of the compound of Formula B by a stable free radical agent to obtain a diaminophenothiazinium compound of Formula A takes place in a single reaction environment, or in a single container or reactor.

It was surprisingly found that the process of the invention allows obtaining diaminophenothiazinium compounds having a high degree of purity in a few steps, mostly without separating the reaction intermediates, with evident advantages in terms of overall speed and environmental and human safety.

As shown in the Examples below, the purity achieved was higher than 95%, preferably higher than 97%.

In particular, the stable free radical agents in acidic aqueous solution tend to disproportionate, by acting as effective oxidizing agents, at the same time remaining in an aqueous solution, thus separating naturally from the diaminophenothiazinium product, which instead precipitates.

This not only increases the purity of the final compound, but makes the process safe, unlike other known oxidizing agents, such as DDQ that in aqueous solutions tends to release highly toxic HCN. Considering that, as said, in the medical field, methylene blue is used as an antidote in case of cyanide poisoning, the use of DDQ is even less appropriate.

The crude diaminophenothiazinium compound of formula A of step 1) is a commercially available product.

Otherwise, the latter may be prepared using the following synthetic route.

The synthesis of MB zds and crude MB provides for the construction of the MB tricyclics structure using N,N-dimethylaniline as a starting material, which is initially converted to N,N-dimethyl-4-nitrosoaniline by treatment with $NaNO_2$ in aqueous HCl at low temperatures.

The nitrous group of N,N-dimethyl-4-nitrosoaniline is reduced to amino group by treatment with zinc powder at low temperatures. Excess zinc is removed by filtration and the mother liquors containing N,N-dimethyl-p-phenylenediamine hydrochloride are directly used in the next step.

Four solutions containing zinc chloride, aluminium sulphate, sodium thiosulfate and chromic acid are sequentially added to the waters of the previous step.

The reaction mixture containing Intermediate 1:

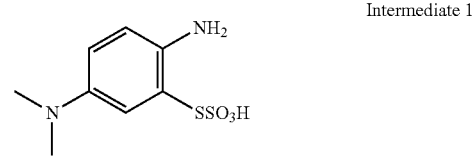

Intermediate 1 is used directly in the next step without further processing.

Two solutions containing N,N-dimethylaniline and chromic acid are sequentially added to the mixture containing Intermediate 1.

The reaction mixture containing Intermediate 2:

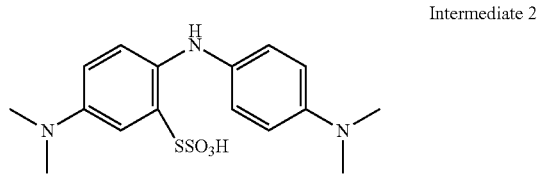

Intermediate 2 is used directly in the next step without further processing.

Manganese dioxide is added to the mixture containing Intermediate 2 and it is heated to allow the final cyclization. The precipitate is recovered by filtration and dissolved in hot water. MB zds is precipitated from the solution by adding zinc chloride and sodium chloride, which is then crystallized by water.

All combinations of preferred aspects of the compounds and of the preparation process given above are to be considered as herein described.

Below are working examples of the present invention provided for illustrative purposes.

EXAMPLES

Example 1. Preparation of Methylene Blue

1) Synthesis of N-benzoyl-Leuco-Methylene Blue (Briefly N-Bz-LMB):

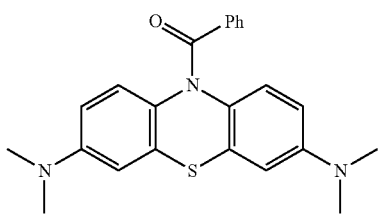

2.5 L water and 250 g methylene blue double salt of zinc are added to a 10 L flask. Under a nitrogen atmosphere, 176 g sodium dithionite are added. It is left under stirring at room temperature for 1 h.

To the same flask, 2.5 L dichloromethane and 25 g tetrabutylammonium bromide are added. 215 g of 32% NaOH and 165 g benzoyl chloride are added dropwise. It is left under stifling for 2 h. 32 g disodium EDTA are added and it is brought to pH 10 with 32% NaOH. It is left under stirring for 1 h. Phases separate. The organic phase is washed with water. The solvent is removed by distillation under vacuum. 2-propanol is added and warmed up at reflux. It is cooled, filtered and dried under vacuum, thus yielding 245 g N-Bz-LMB.

2) Oxidation of Methylene Blue (Briefly MB):

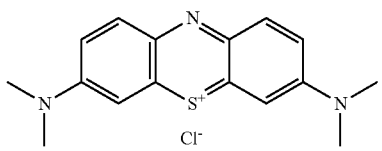

90 mL water and 310 g of 37% HCl are added to a 3 L flask. It is cooled to about −5° C. 70 g N-Bz-LMB are added. 173 g of a 40% by weight aqueous solution of 4-hydroxy TEMPO are added dropwise over 2 h keeping the temperature at −5° C. It is left under stirring for 1 h. 1.12 L water and 400 mL methyl isobutyl ketone are added and it is left under stirring at room temperature for 2 h. The solid is filtered and washed with 0.1N HCl. The wet product and 1.6 L water are added to a suitable flask. It is heated to 65° C., then it is rehydrated at room temperature. The pH is adjusted to 1 with 37% HCl and it is left under stirring for 16 h. The solid is filtered and washed with 0.1N HCl. It is dried under vacuum, thus yielding 50 g MB.

The MB product thus obtained has the following features: Purity: 97.8%, Azure B: 2.2%, metal content within the limits set by the European Pharmacopoeia 8.0, loss on drying: 14%.

The data obtained are according to the specifications defined by the current Pharmacopoeias.

Example 2. Preparation of Methylene Blue

1) Synthesis of N-benzoyl-Leuco-Methylene Blue:
The process was as in Example 1, using crude methylene blue as a starting material instead of MB zds.
2) Oxidation of Methylene Blue:
The process was as in Example 1.
The MB product thus obtained has a 97.9% purity.

Example 3. Preparation of Methylene Blue

1) Synthesis of N-benzoyl-Leuco-Methylene Blue:
The process was as in Example 1, by using crude methylene blue as a starting material instead of MB zds.
2) Oxidation of Methylene Blue:
The process was as in Example 1, by using TEMPO instead of 4-hydroxy TEMPO, in a 20% by weight aqueous solution.
The MB product thus obtained has a 97.7% purity.

Example 4. Preparation of Methylene Blue

1) Synthesis of N-benzoyl-Leuco-Methylene Blue:
The process was as in Example 1, by using crude methylene blue as a starting material instead of MB zds.
2) Oxidation of Methylene Blue:
The process was as in Example 1, by using AZADO instead of 4-hydroxy TEMPO, in a 25% by weight acidic aqueous solution.
The MB product thus obtained has a 97.6% purity.

Example 5. Preparation of Methylene Blue

1) Synthesis of N-benzoyl-Leuco-Methylene Blue:
The process was as in Example 1, by using crude methylene blue as a starting material instead of MB zds.
2) Oxidation of Methylene Blue:
The process was as in Example 1, by using 4-hydroxy TEMPO in a 20% by weight aqueous solution.
The MB product thus obtained has a 97.5% purity.

Example 6. Preparation of Methylene Blue

1) Synthesis of N-benzoyl-Leuco-Methylene Blue:
The process was as in Example 1.
2) Oxidation of Methylene Blue:
The process was as in Example 1, by using 4-hydroxy TEMPO in a 30% by weight aqueous solution.
The MB product thus obtained has a 97.8% purity.

Example 7. Preparation of Methylene Blue

1) Synthesis of N-benzoyl-Leuco-Methylene Blue:
The process was as in Example 1.
2) Oxidation of Methylene Blue:
The process was as in Example 1, by using NHAc-TEMPO instead of 4-hydroxy TEMPO, in a 20% by weight aqueous solution.
The MB product thus obtained has a 97.8% purity.

Example 8. Preparation of Methylene Blue

1) Synthesis of N-benzoyl-Leuco-Methylene Blue:
The process was as in Example 1.
2) Oxidation of Methylene Blue:
The process was as in Example 1, by using 3-carbamoyl-proxyl instead of 4-hydroxy TEMPO, in a 20% by weight aqueous solution.
The MB product thus obtained has a 97.1% purity.

The invention claimed is:
1. Process for the preparation of diaminophenothiazinium compounds of formula A having a degree of purity higher than 95%, said process comprising the steps of:
1) providing a crude diaminophenothiazinium compound of formula A:

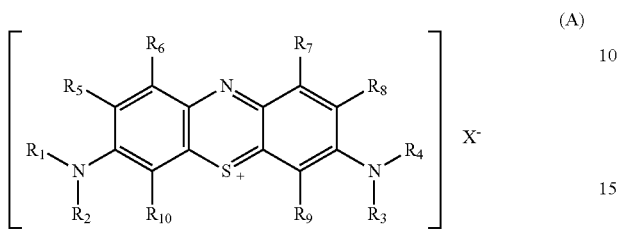

(A)

wherein $R_1$, $R_2$, $R_3$, $R_4$ are, independently of one another,
a saturated or unsaturated, linear, branched, or cyclic, C1-C6 alkyl group, optionally substituted with one or more functional groups selected from a halogen atom, a C1-C4 alkoxy, a C1-C4 alkyloxycarbonyl, or —$CONH_2$,
an aryl group optionally substituted with one or more functional groups selected from a C1-C4 alkyl group, a halogen atom, a C1-C4 alkoxy, a C1-C4 alkyloxycarbonyl, or —$CONH_2$, or
a hydrogen atom,
$R_5$, $R_6$, $R_7$, $R_8$, $R_9$, $R_{10}$ is selected, independently of one another, from
a hydrogen atom,
a saturated or unsaturated, linear, branched, or cyclic, C1-C6 alkyl group, optionally substituted with one or more functional groups selected from a halogen atom, a C1-C4 alkoxy, a C1-C4 alkyloxycarbonyl, or —$CONH_2$,
an aryl group optionally substituted with one or more functional groups selected from a C1-C4 alkyl group, a halogen atom, a C1-C4 alkoxy, a C1-C4 alkyloxycarbonyl, or —$CONH_2$, or
a halogen atom,
and wherein X– is an organic or inorganic anion,
2) synthesizing a compound of formula B:

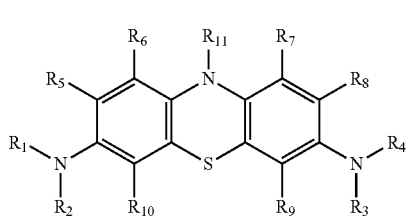

(B)

wherein $R_1$-$R_{10}$ are as in the formula A,
$R_{11}$ is
a hydrogen atom,
a carbonyl or thiocarbonyl group functionalized with
a phenyl or benzyl group, optionally substituted with C1-C4 alkyl groups, a halogen atom, C1-C4 alkoxy, or a nitro group,
a linear, branched or cyclic C1-C8 alkyl group,
a C1-C8 alkylamino group,
a C1-C8 alkoxy group, or
a phenyloxy or benzyloxy group, optionally substituted on the aromatic ring with C1-C4 alkyl groups, a halogen atom, C1-C4 alkoxy, or a nitro group,
by reaction of the crude diaminophenothiazinium compound of formula A with a reducing agent and a protective agent comprising the group $R_{11}$, and
3) obtaining the diaminophenothiazinium compound of the Formula A having a degree of purity higher than 95%, through oxidation of the compound of the Formula B by a stable free radical agent, said stable free radical agent being proxyl (2,2,5,5-tetramethyl-1-pyrrolidinyloxy), 3-carboxyl-proxyl, 3-carbamoyl-proxyl, 2,2-dimethyl-4,5-cyclohexyl-proxyl, 3-oxo-proxyl, 3-hydroxylimine-proxyl, 3-aminomethyl-proxyl, 3-methoxy-proxyl, 3-t-butyl-proxyl, 3-maleimido-proxyl, 3,4-di-t-butyl-proxyl, 3-carboxylic-2,2,5,5-tetramethyl-1pyrrolidinyloxy, TEMPO (i.e. 2,2,6,6-tetramethyl-1-piperidinyloxy), NHAc-TEMPO, 4-C1-6-alkyloxy-TEMPO, 4-benzoxyloxy-TEMPO, 4-methoxy-TEMPO, 4-carboxylic-4-amino-TEMPO, 4-chloro-TEMPO, 4 hydroxylimine-TEMPO, 4-hydroxy-TEMPO, 4-oxo-TEMPO, 4-oxo-TEMPO-ethylene ketal, 4-amino-TEMPO, 2,2,6,6-tetraethyl-1-piperidinyloxy, 2,2,6-trimethyl-6-ethyl 1-piperidinyloxy, di-t-butyl nitroxide, di-t-butyl nitroxyl, diphenyl nitroxide, diphenyl nitroxyl, t-butyl-t-amyl nitroxide, DOXYL (4,4-dimethyl-1-oxazolidinyloxy), 2-di-t-butyl-doxyl, 5-decane-doxyl, 2-cyclohexane-doxyl, 2,5-dimethyl-3,4-dicarboxylic-pyrrole, 2,5-dimethyl-3,4-diethylester-pyrrole, 2,3,4,5-tetraphenyl-pyrrole, 3-cyano-pyrroline-3-carbamoyl-pyrroline, 3-carboxylic-pyrroline, 1,1,3,3-tetramethylisoindoline-2-yloxyl, 1,1,3,3-tetraethylisoindolin-2-yloxyl, 5-cyclohexyl porphyrexide nitroxyl, 2,2,4,5,5-pentamethyl-[DELTA]3-imidazoline-3-oxide-1-oxyl, galvinoxyl, 1,3,3-trimethyl-2-azabicyclo[2,2,2]octane-5-one-2-oxide, 1-azabicyclo[3,3,1]nonane-2-oxide, 2-Azaadamantane N-Oxyl (AZADO), 9-Azabicyclo[3.3.1]nonane N-oxyl (ABNO), 9-Azanoradamantane N-oxyl (Nor-AZADO), or a mixture thereof.
2. The process of claim 1, wherein said crude diaminophenothiazinium compound of formula A is crude Methylene blue, Methylene Blue zinc double salt or a mixture thereof.
3. The process of claim 1, wherein step 3) is a one-pot synthesis step.
4. The process of claim 1, wherein said stable free radical agent is TEMPO, NHAc-TEMPO, 4-C1-6-alkyloxy-TEMPO, 4-benzoxyloxy-TEMPO, 4-methoxy-TEMPO, 4-carboxylic-4-amino-TEMPO, 4-chloro-TEMPO, 4 hydroxylimine-TEMPO, 4-hydroxy-TEMPO, 4-oxo-TEMPO, 4-oxo-TEMPO-ethylene ketal, 4-amino-TEMPO, 2,2,6,6-tetraethyl-1-piperidinyloxy, 2,2,6-trimethyl-6-ethyl 1-piperidinyloxy, 1,3,3-trimethyl-2-azabicyclo[2,2,2]octane-5-one-2-oxide, 1-azabicyclo[3,3,1]nonane-2-oxide, 2-Azaadamantane N-Oxyl (AZADO), 9-Azabicyclo[3.3.1]nonane N-oxyl (ABNO), 9-Azanoradamantane N-oxyl (Nor-AZADO), or a mixture thereof.
5. The process of claim 4, wherein said stable free radical agent is TEMPO, NHAc-TEMPO, 4-methoxy-TEMPO, 4-carboxylic-4-amino-TEMPO, 4-chloro-TEMPO, 4 hydroxylimine-TEMPO, 4-hydroxy-TEMPO, 4-oxo-TEMPO, 4-amino-TEMPO, 2-Azaadamantane N-Oxyl (AZADO), 9-Azabicyclo[3.3.1]nonane N-oxyl (ABNO), 9-Azanoradamantane N-oxyl (Nor-AZADO), or a mixture thereof.
6. The process of claim 5, wherein said stable free radical agent is TEMPO, 4-hydroxy-TEMPO, 2-Azaadamantane N-Oxyl (AZADO), or a mixture thereof.

7. The process of claim 6, wherein said stable free radical agent is 4-hydroxy-TEMPO.

8. The process of claim 1, wherein said stable free radical agent is the only oxidant agent used in step 3).

9. The process of claim 1, wherein, at the end of step 3), the resulting product is recovered from the reaction mixture by precipitation and washing.

10. The process of claim 1, wherein in step 3) said stable free radical agent is added as an aqueous solution comprising up to 60% by weight of stable free radical agent, preferably comprising 10-50% by weight of stable free radical agent.

11. The process of claim 1, wherein said degree of purity higher than 97%.

* * * * *